(12) United States Patent
Al-Salloum et al.

(10) Patent No.: US 9,341,553 B2
(45) Date of Patent: May 17, 2016

(54) APPARATUS FOR ASSESSING DURABILITY OF STRESSED FIBER REINFORCED POLYMER (FRP) BARS

(71) Applicant: King Saud University, Riyadh (SA)

(72) Inventors: Yousef A. Al-Salloum, Riyadh (SA); Tarek H. Almusallam, Riyadh (SA); Saleh H. Alsayed, Riyadh (SA); Husain Abbas, Riyadh (SA)

(73) Assignee: King Saud University, Riyadh (SA)

( * ) Notice: Subject to any disclaimer, the term of this patent is extended or adjusted under 35 U.S.C. 154(b) by 61 days.

(21) Appl. No.: 14/274,796

(22) Filed: May 12, 2014

(65) Prior Publication Data

US 2015/0323433 A1    Nov. 12, 2015

(51) Int. Cl.
*G01N 3/08* (2006.01)

(52) U.S. Cl.
CPC ........................................ *G01N 3/08* (2013.01)

(58) Field of Classification Search
CPC .................. G01N 3/08; G01N 17/002; G01N 2203/0096; F16G 11/02; F16G 11/048; F16G 11/04; Y10T 403/7039; Y10T 403/7052; E04C 5/085; E04C 23/046; E04C 5/07

USPC ................. 73/54.23, 828; 264/228; 52/223.4, 52/223.13–14

See application file for complete search history.

(56) References Cited

U.S. PATENT DOCUMENTS

| 4,648,224 A | 3/1987 | Kitta et al. |
| 5,131,265 A | 7/1992 | Tobin et al. |
| 5,802,788 A | 9/1998 | Ozawa et al. |
| 6,832,454 B1 | 12/2004 | Iyer |
| 7,056,463 B2 | 6/2006 | Ohta |

FOREIGN PATENT DOCUMENTS

CN    103267724    *    8/2013    ............. G01N 19/04

* cited by examiner

*Primary Examiner* — Lisa Caputo
*Assistant Examiner* — Brandi N Hopkins
(74) *Attorney, Agent, or Firm* — Hauptman Ham, LLP

(57) ABSTRACT

An apparatus for testing a specimen consisting of a fiber reinforced polymer (FRP) bar in tension while embedded in hardened concrete and subjected to long term environmental exposure. The apparatus includes a steel channel defined by two longitudinally extending parallel steel plates and a pair of unitary plates with one unitary plate at each of the channel. Each of the unitary plates include a U-shaped opening while a forward one of the unitary plates also defines four threaded openings and four bolts passing therethrough for increasing strain on the specimen. A pair of steel tube grips attached to the FRP bar with epoxy are also provided.

4 Claims, 4 Drawing Sheets

APPARATUS FOR ASSESSING DURABILITY OF STRESSED FIBER REINFORCED POLYMER (FRP) BARS

FIELD OF THE INVENTION

This invention relates to an apparatus for assessing the durability of stressed fiber reinforced polymer (FRP) bars and more particularly to the testing of stressed fiber reinforced polymer bars embedded in concrete during long term environmental exposure.

BACKGROUND OF THE INVENTION

It is often desirable to study the effect of environmental exposure on FRP bars under a stressed state while embedded in concrete. This requires investigating the behavior of structural elements reinforced with FRP bars and involves large scale materials and labor. Further the transportation of such specimens for environmental exposure is difficult. In addition, because of the high strength of FRP bars, the testing of such reinforcing bars up to failure requires large spans and a high magnitude of gravity loads.

In view of the aforementioned difficulties, long-term durability studies under stressed state representing the actual exposure of loading are not widely reported in the literature. However, a patent search did disclose a U.S. Patent of Kitta et al. U.S. Pat. No. 4,648,224. As disclosed therein, a tendon for prestressed concrete wherein inorganic particles are coated on an outer surface of a rod made of fiber reinforced plastic through a plastic adhesive layer. The inorganic particles are formed with minute rugged surface portions on the outer surface of the tendon for prestressed concrete, the rugged surface portions being firmly adhered to concrete. The inorganic particles are coated on the whole outer surface of the tendon for prestressed concrete, on the fixed portions at both ends, and on a portion subjected to the maximum bending moment. The reference teaches that samples are prestressed to 70% of the breaking load in a mold and concrete introduced into the mold. After hardening, prestressing grips are released and a strain gauge on the surface of the concrete measures surface strain at various points.

A more recent U.S. Pat. No. 7,056,463 of Ohta discloses a method of manufacturing prestressed concrete. As disclosed, pre-tension and post-tension processes for the manufacture of pre-stressed structures in which bonded carbon fiber cables are provided with burial anchors and temporary anchors outward of the burial anchors. The burial anchors are embedded in the structure. The temporary anchors enable stressing of the carbon fiber cables.

It is presently believed that the present invention provides a solution to the above-identified problems by developing a new apparatus for preparing representative small size specimens for testing FRP bars embedded in concrete under a stressed state and during relatively long-term environmental exposure. The desired stress level in FRP bars can be easily maintained during the period of investigation.

SUMMARY OF THE INVENTION

In essence, the present invention contemplates an apparatus for testing FRP bars in tension after environmental exposure while embedded in concrete in a stressed state.

The apparatus in accordance with the invention comprises or consists of:

a.) a steel channel section with a U-shaped opening on each end of the channel;

b.) four bolts and nuts at a first of said U-shaped openings for positioning and stressing an FRP bar embedded in hardened concrete; and c.) a pair of threaded steel tube grips at the two ends of the FRP bar with said FRP bar ends bonded to said threaded steel tubes using epoxy.

In a preferred embodiment of the invention the channel section includes a first pair of longitudinally extending parallel steel plates extending along and slightly beyond the ends of the FRP bar in close proximity to a specimen and a second pair of relatively short outwardly extending steel plates perpendicular to the first pair of steel plates.

A first unitary plate disposed forwardly of the second pair of parallel plates that include a U-shaped opening extending from a topside thereof to slightly beyond the center of the first unitary plate and four threaded openings in the first unitary plate and four threaded nuts welded, or fixed as for example welded, braised or soldered to a front surface of the first unitary plate. The four threaded bolts are screwed into the four threaded openings and passed therethrough rearwardly into a butting relationship with the second pair of outwardly extending plates.

The preferred embodiment of the invention also includes a second unitary plate extending perpendicular across the first pair of steel plates and defining a U-shaped opening extending from a top side thereof to slightly beyond a center thereof and wherein the U-shaped opening in said second unitary plate is adapted to have a second one of the steel tube grips extending therethrough with a large nut thereon for tightening against the second unitary plate to fixedly position the specimen within the channel.

At a first end of the channel a first of the steel tube grips extending through the U-shaped openings in the first unitary plate with a large nut on the first of the steel tube grips for subjecting the specimen to a preselected strain or stress; and a gauge for indicating the stress on the FRP bar.

The invention will now be described in connection with the following drawings.

DESCRIPTION OF THE PREFERRED EMBODIMENTS OF THE INVENTION

The present invention provides a practical solution for replacing the costly and labor intensive testing of full scale FRP reinforcing bars while embedded in concrete and exposed to atmospheric conditions under stress for relatively long periods of time.

Figure 1A:
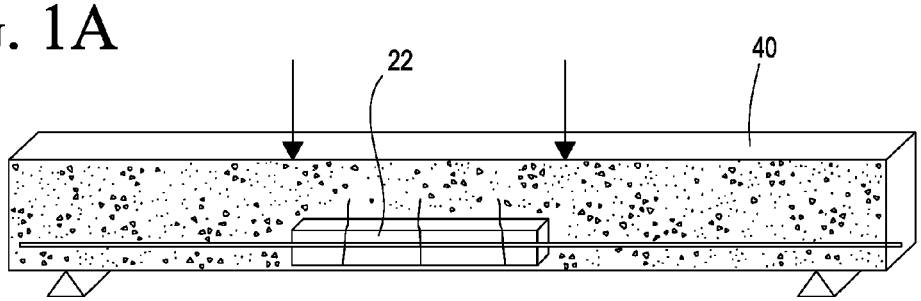
FIG. 1A illustrates a conventional four point flexure test for a reinforced concrete beam with a representative FRP bar specimen at the centroid of a concrete section to be investigated.
Figure 1B:
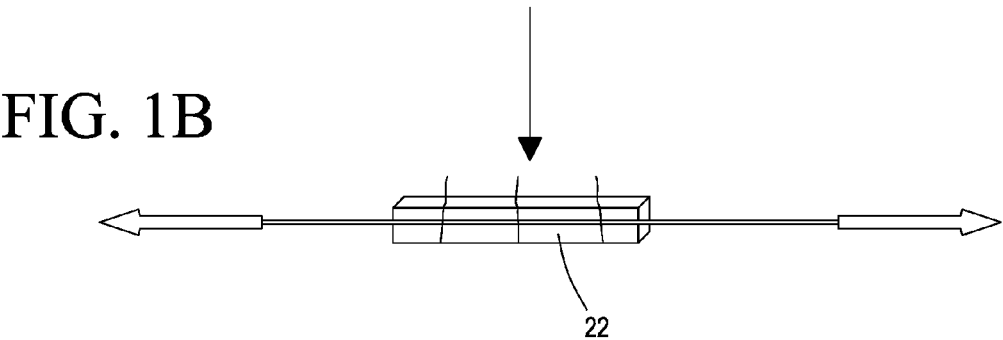
FIG. 1B is a schematic illustration of stress applied to the drawing in FIG. 1A.

As illustrated in FIG. 1A, a reinforced concrete beam 2 is subjected to standard four point flexure test with a representative element 4 in the flexure zone. The representative element with rebar at the centroid of concrete to be investigated is shown in FIG. 1B.

Figure 2:
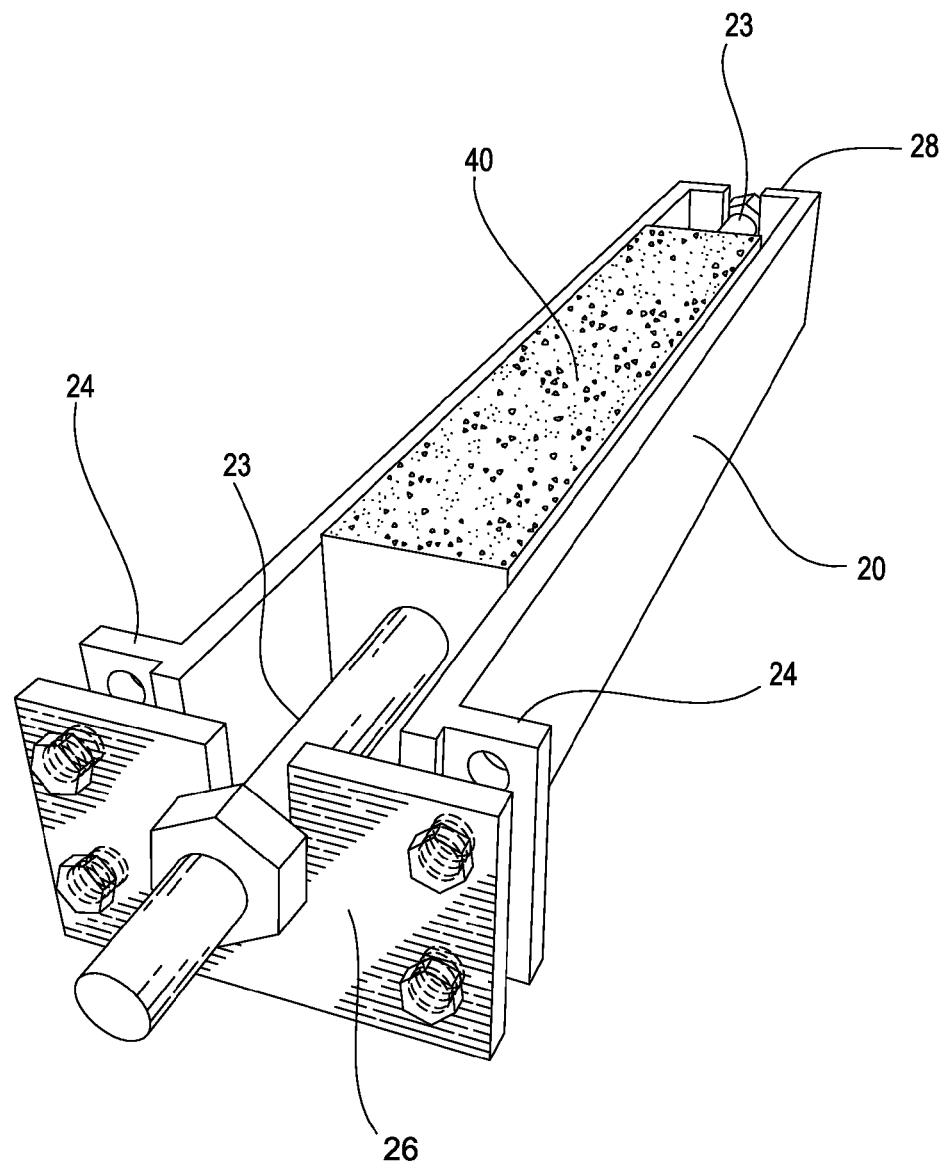
FIG. 2 is an isometric view of a preferred embodiment of the invention.

Referring now to FIG. 2, an apparatus for assessing the durability of a stressed fiber reinforced polymer (FRP) bars or test specimen 22 as embedded in concrete during long term environmental exposure as shown by encasement 40. As illustrated, a first pair of longitudinally extending parallel steel plates 20 extend along and closely engage opposite ends of a concrete encased FRP bar of a specimen 22. The cross section is preferably a square in the preferred embodiment, other cross sections of the specimen may have other shapes such as circular.

The specimen 22 also includes a pair of steel tube grips 23. Both steel tube grips are bonded at each end of an FRP bar of the specimen 22 and bonded thereto using epoxy.

A second pair of relatively short outwardly extending steel plates 24 are fixed at or quite near a forward end of the first pair of parallel steel plates and are perpendicular thereto. In addition, a first unitary plate 26 is disposed forwardly of the second pair of steel plates relatively near the ends of the first pair of steel plates 20 and generally perpendicular thereto and parallel to the second pair of steel plates.

The first unitary plate 26 defines a generally U-shaped opening extending downwardly from a top of the first unitary plate 26 to shortly beyond the center thereof. The first unitary plate 26 also defines four threaded openings with one of the openings in each corner and includes four threaded nuts fixed to a front surface of the plate 26 and in alignment with the four openings. The four threaded nuts may be welded, braised or soldered to the front surface of the unitary plate.

A second unitary plate 28 extends inwardly between said first pair of steel plates 20 and are fixed to the far ends of the pair of plates 20 as for example by welding. The second unitary plate 28 also includes a downwardly extending U-shaped opening extending from an upper edge thereof to slightly past the center thereof. The U-shaped openings in the first and second unitary plates are sized to accommodate the steel tube grips with close tolerances so that a relatively large nut and washer (washer not shown in FIG. 2) on an outer end of the steel tube grip from passing through the U-shaped opening. A relatively large nut on the forward end of the channel may also be used to adjust the stress on the FRP bar.

Figure 3:
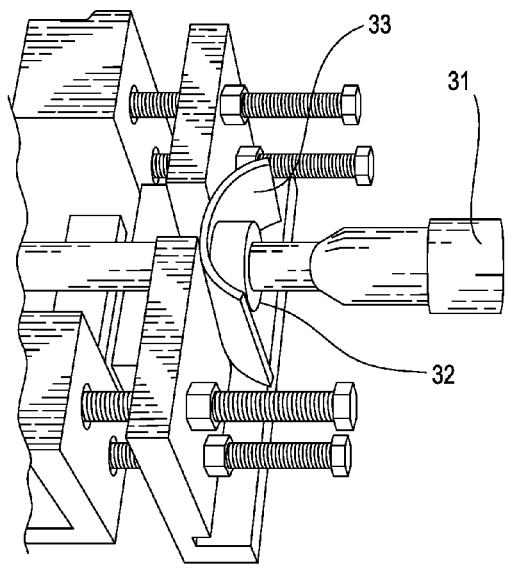
FIG. 3 is a schematic illustration of a collar end of the embodiment shown in FIG. 2 and illustrating the application of stress or strain.

As illustrated in FIG. 3, a cap 31 (for protecting FRP bar ends) is fixed at the end of the steel tube grip rearwardly of a large nut 32 and oversize plate like washer 33. As shown, the four threaded bolts are used to increase the strain on the specimen by forcing the first unitary plate away from the second pair of outwardly extending plates.

Figure 4:
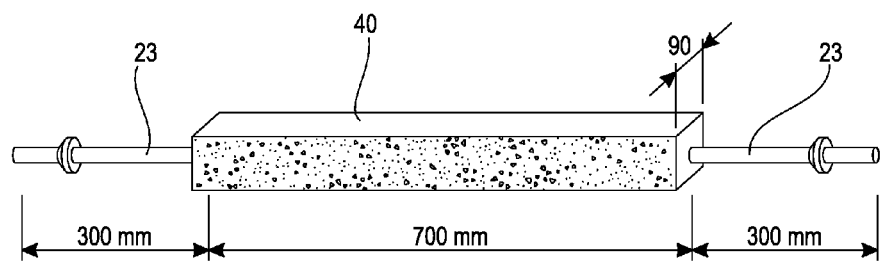
FIG. 4 is a schematic illustration of the concrete test specimen with a centrally embedded FRP bar and exemplary dimensions.
Figure 5:
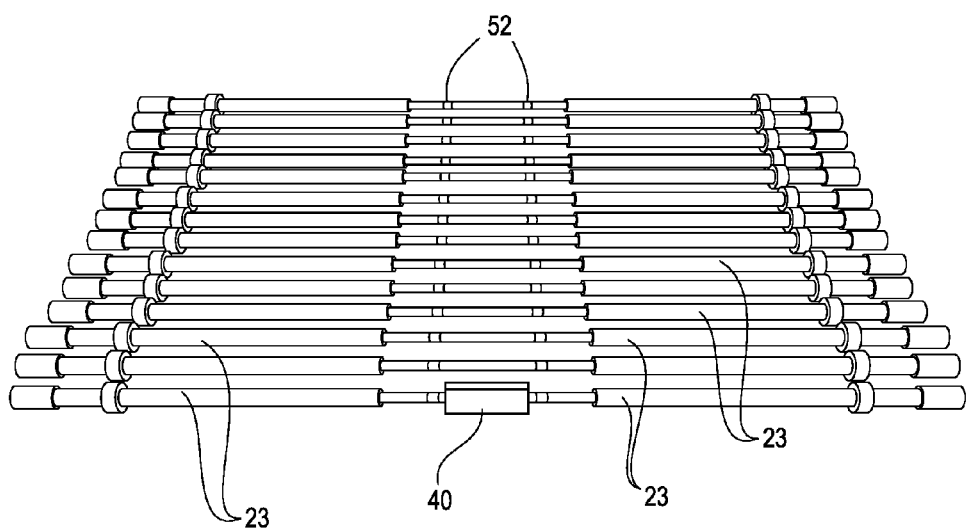
FIG. 5 is a schematic illustration of a plurality of instrumented FRP bars with steel tube grips at their ends before embedding in concrete.

A concrete encasement 40 with a centrally embedded FRP bar (not shown) and a pair of steel tube grips 23 extend outwardly therefrom with large threaded nuts thereon and exemplary dimensions is illustrated in FIG. 4. As shown, the concrete encasement 40 has a square cross section wherein each side is about 90 mm in length and the concrete section has a length of about 700 mm. The steel tube grips extend outwardly about 300 mm from each end of the encasement 40.

A plurality of FRP bar test specimens with steel tube grips 23 and strain gauges 52 are ready for embedment in concrete.

While the invention has been described in connection with its accompanying drawings, it should be recognized that changes and modifications may be made therein without departing from the scope of the appended claims.

What is claimed is:

1. An apparatus for testing durability of stressed fiber reinforced polymer (FRP) bars in tension encased in hardened concrete after long term environmental exposure by maintaining the bars in a stressed state during such exposure, in which said apparatus comprising:
    a) a steel channel section with a U-shaped opening on each end of said channel;
    b) four bolts and nuts at a first of said U-shaped openings for positioning and stressing an FRP bar embedded in hardened concrete; and
    c) a threaded steel tube and a threaded steel tube grip at each of the two ends of the FRP bar with FRP bar bonded to said threaded steel tubes using epoxy;
    in which
    said channel section including a first pair of longitudinally extending parallel steel plates extending along and slightly beyond the ends of a specimen of a FRP bar encased in hardened concrete and in close proximity to said specimen and a second pair of relatively short steel plates extending outwardly from and perpendicular to said first pair of steel plates;
    a first unitary plate disposed forwardly of said second pair of relatively short plates and said first unitary plate including a U-shaped opening extending from a top thereof to slightly beyond the center thereof and four threaded openings in said first unitary plate, and four threaded bolts extending through said four threaded openings in a rearward direction and abutting said second pair of outwardly extending plates;
    a second unitary plate extending inwardly across said first pair of steel plates and perpendicular to said first pair of steel plates, and said second unitary plate defining a U-shaped opening extending downwardly from the top side of said second unitary plate to slightly beyond the center of said second unitary plate and wherein said second unitary plate is fixed to the ends of said first pair of steel plates;
    a strain gauge disposed at one outer end of one of said steel tube grips and a large nut disposed on each of said steel tube grips to fix said specimen between said unitary plates under moderate strain; and
    wherein extending said threaded bolts through said threaded openings in said first unitary plate against said second pair of relatively short outwardly extending plates increases the stress on the specimen to a preselected level.

2. The apparatus for testing durability of stressed fiber reinforced polymer (FRP) bars in tension encased in hardened concrete after long term environmental exposure by maintaining the bars in a stressed state during such exposure according to claim 1, in which said hardened concrete encasing the FRP bar has a square cross section.

3. An apparatus for testing durability of stressed fiber reinforced polymer (FRP) bars in tension encased in hardened concrete after long term environmental exposure by maintaining the bars in a stressed state during such exposure, said apparatus consisting of:
    a) a steel channel section including a first pair of longitudinally extending steel plates with a U-shaped opening on each end thereof;
    b) four bolts and nuts at a first end of said U-shaped openings for applying preselected stress in a FRP bar embedded in hardened concrete;
    c) threaded steel tubes and threaded steel tube grips at the ends of the FRP bar with the FRP bar bonded to said threaded steel tubes using epoxy;

d) said steel channel section including said first pair of longitudinally extending steel plates extending along and slightly beyond the ends of a specimen of a FRP bar encased in concrete and in close proximity to said specimen; and e) a second pair of relatively short steel plates extending outwardly from and perpendicular to said first pair of steel plates; and wherein f) said four bolts extending rearwardly toward said second pair of plates;

g) a first unitary plate disposed forwardly of said second pair of plates and including one of said U-shaped openings extending from one side thereof to slightly beyond the center of said first unitary plate and four openings in said first unitary plate for allowing said four bolts to pass therethrough;

h) a second unitary plate defining a U-shaped opening extending from one side thereof to slightly beyond the center thereof and wherein said U-shaped opening in said second unitary plate is adapted to have one of said threaded steel tube grips extending therethrough with a large nut threaded thereon for tightening against said second unitary plate to fixedly position a specimen within said channel;

i) at a first end of said channel a first of said steel tube grips extending through said U-shaped opening in said first unitary plate with a large nut on said steel tube grip for subjecting said specimen to preselected stress; and j) wherein loosening said four bolts against said second pair of plates increases the strain on said FRP bar.

4. A method for testing durability of a stressed fiber reinforced polymer (FRP) bar encased in hardened concrete after long term environmental exposure, said method consisting of:

providing a specimen of a FRP bar and encasing the specimen in concrete;

providing an apparatus for testing durability of said specimen;

subjecting said specimen to a preselected degree of stress;

maintaining the preselected stress for a preselected period of time; and determining the condition of the specimen after the preselected exposure.

* * * * *